US005843782A

United States Patent [19]
Dobres et al.

[11] Patent Number: 5,843,782
[45] Date of Patent: Dec. 1, 1998

[54] MICROPROPAGATION OF ROSE PLANTS

[75] Inventors: Michael Dobres, Philadelphia, Pa.; Gail R. Williams Lokaj, Wenonah, N.J.

[73] Assignee: NovaFlora, Inc., Philadelphia, Pa.

[21] Appl. No.: 385,772

[22] Filed: Feb. 9, 1995

[51] Int. Cl.$^6$ .................................................. G12M 5/00
[52] U.S. Cl. ....................... 435/430; 435/410; 435/420; 435/431
[58] Field of Search ........................... 435/240.45, 240.4, 435/240.48, 240.49, 240.54, 410, 420, 430, 431

[56] References Cited

U.S. PATENT DOCUMENTS

P.P. 7,021  9/1989  Meilland ................................... Plt./10

FOREIGN PATENT DOCUMENTS

WO 92/00371  1/1992  WIPO.

OTHER PUBLICATIONS

Hasegawa *J. Amer Hort. Sci* 105 (2) 216–220. 1980.
Murashige et al. *Physiologian Plantarum*. vol 15.1962 p. 473.
Gamborg et al. *Exp. Cell Research*. 50. 1968 pp. 151–158.
Shenk et al., Medium and techniques for induction and growth of monocotyledonous and dicotyledonous plant cell cultures *Can. J. Bot*, vol. 50, pp. 199–204 1972.
Murashige et al., A Revised Medium for Rapid Growth and Bio Assays with Tobacco Tissue Cultures *Physiol. Plant.*, vol. 15, pp. 473–497 1962.
Huang et al., Plant Tissue Culture Media, TCA Manual, vol. 3, pp. 539–548.
Gamborg et al., Nutrient Requirements of Suspension Cultures of Soybean Root Cells *Exp. Cells Res.* 1968, 50, 151–158.
Chu et al. Commercialization of Plant Micropropagation Handbook of Plant Cell Culture vol. 5 Chapter 6 Ammirator Ed. 1983 126–164.
Hasegawa P. Factors Affecting Shoot and Root Initiation from Cultured Rose Shoot Tips *J. Amer. Soc. Hort. Sci.* 1980 105:216–220.
Arene et al. A comparison of the somaclonal variation level of *Rosa hybrida* L. cv Meirutral plants regenerated from callus or direct induction from different vegetative and embryonic tissues *Euphytica* 1993 71:83–90.
George J. NovaFlora 's Flowers are created to improve on Mother Nature *Philadelphia Business Journal* Feb 10–16, 1995 13:1&10.
Davies D. Rapid Propagation of Roses in Vitro *Scientia Horticulturae* 1980 13:385–389.
Woltering E. Beneficial effects of carbon dioxide on development of gerbera and rose plantlets grow in vitro *Scientia Horticulturae* 1990 44:341–345.
Kunitake et al. Somatic embryogeneisis and plant regeneration from immature seed–derived calli of rugose rose *Plant Science* 1993 90:187–194.
Rout et al. Somatic embryogenesis in callus cultures of Rosa hybrida L. cv. Landora *Plant Cell Tissue and Organ Culture* 1991 27:65–69.

Ghashghaie et al. Effects of agar concentration on water status and growth of rose plants cultured in vitro *Physilogia Plantarium* 1991 82:73–78.
Lloyd et al. The induction in vitro of adventitious shoots in Rosa *Euphytica* 1988 37:31–36.
Van der Salm et al. Importance of the iron chelate formula for micropropagation of Rose Hybrida L. 'Moneyway' *Plant Cell Tissue and Organ Culture* 1994.
Delbard H. Micropropagation of Rose at Delbard Nurseries Abstract *The Plant Propagator* 1982.
Khosh–Khui et al. Rooting–Enhancement of Rosa Hybrida for Tissue Culture Propagation *Scientia Horticulturae* 1982 17:371–376.
Vijaya et al. Effect of culture media and growth regulators on in vitro propagation of rose *Current Plant Sci. and Biotech. in Agric.* 1991 12:209–214.
Campos et al. Mass propagation of the dwarf rose cultivar "Rosamini" *Scientia Horticulturae* 1990 43:321–330 Abstract.
Bressan et al. Factors Affecting in Vitro Propagation of Rose *J. Amer. Soc. Hort. Sci.* 1982 107 :979–990.
Skirvin et al. In Vitro Propagation of Forever Yours Rose *HortScience* 1979 14:608–610.
Hasegawa P. In Vitro Propagation of Rose *HortScience* 1979 14:610–612.
Arnold et al. A study of the effect of growth regulators and time of plantlet harvest on the in vitro multiplication rate if hardy and hybrid tea roses *Jour. Hort Sci* 1992 67:727–735.
DeVries et al. The Effect BAP and IBA on Sprouting and Adventitious Root Formation of 'Amanda' Rose Single–Node Softwood Cuttings *Scientia Horticulturae* 1988 34:115–121.
Douglas et al. Micorpropagation of floribunda, ground cover and miniature roses *Plant Cell Tissue and Organ Culture* 1989 19:55–64.

(List continued on next page.)

*Primary Examiner*—Leon B. Lankford, Jr.
*Attorney, Agent, or Firm*—Woodcock Washburn Kurtz Mackiewicz & Norris LLP

[57] ABSTRACT

The present invention is directed to, inter alia, a method of micropropagation of a rose plant comprising culturing a stem bearing a node in a first enclosed vessel containing a first culture medium comprising about 0.5 to about 3.0 mg/l of a cytokine, 0 to about 1.0 mg/l of an auxin, and 0 to about 1.0 mg/l of a gibberellin until at least one shoot emerges from the node; excising the shoot from the stem and propagating the shoot in a second enclosed vessel containing a second culture medium comprising about 0.5 to about 3.0 mg/l of a cytokine, 0 to about 1.0 mg/l of an auxin, and 0 to about 1.0 mg/l of a gibberellin to produce a flowering rose plant capable of being transferred to soil. Among other things, the present invention is also directed to rose plants and culture media for the micropropagation of roses.

55 Claims, 7 Drawing Sheets

(7 of 7 Drawing Sheet(s) Filed in Color)

OTHER PUBLICATIONS

Khosh–Khui et al. Micropropagation of new and old world rose specie *Jour. Hort. Sci.* 1982 57: 315–319.

McIver J. Man Propagates Plenty of Plants in Pembroke Park The Miami Herald Feb. 7, 1985 BSW:23.

Gallagher C. Grower Find a Demand For Bright Flowers The Miami Herald Jan 31, 1988 4H.

Henderson D. Nurseryman Breeds Plants in Test Tubes Friends, Experts Praise Researcher on the Move The Miami Herald Apr 11, 1990 1BR.

Oglesby R. Noted Nurseryman Now Town Commissioner The Miami Herald Oct 30, 1990 4BR.

Selinker M. Horticulturalist Builds A Better Banana He Is Recognized As Leader in Field Sun Sentinel The Miami Herald Mar 6, 1988 SE:3.

Brookwell J. House Plants Enjoy a Breath of Air Aug 14, 1992 1E.

MICROPROPAGATION OF ROSE PLANTS

BACKGROUND OF THE INVENTION

Micropropagation, also known as axillary bud propagation or in vitro asexual propagation, is one of a number of methods known in the art for the propagation of desirable species or varieties of plants. Other traditional methods of asexual propagation include greenhouse and field propagation of plant cuttings. There are many advantages, however, which favor micropropagation as a propagative method of choice. One advantage is that a plant which has a known and desirable phenotype can be chosen as the source of cells, and, in accordance with micropropagation techniques, these cells can be rapidly cultured into many genetically uniform plantlets. The resulting plantlets may then be cultivated into entire plants possessing roots and shoots. Thus, in accordance with this technique, plants with the same desirable phenotype as the parent can be mass produced, potentially at costs comparable to and often more quickly than standard greenhouse or field methods of asexual propagation.

The propagation of plants under sterile aseptic conditions has been used as cost effective means for the mass propagation of certain plants. An important consideration of this technology is the ability to add value to plants being propagated. In many cases value is added by assuring uniformity of product, and products that are free of bacterial, fungal, viral, or insect pests.

Commercial propagation of roses is normally carried out by budding or grafting of a specific shoot cutting, or scion, onto an established wild rose root stock. In recent years numerous publications have dealt with the propagation of roses through tissue culture. Examination of the literature reveals that different varieties and types display greatly varying nutrient and hormone requirements. Indeed, the process of producing plants from explants or plant tissues, however, requires the development of a culture medium and protocol suitable for the particular type of plant tissue. Various media and procedures have been attempted, but only some have been met with success. For this reason, most commercial growers of roses still propagate rose plants by traditional means.

For example, Hasegawa, *J. Amer. Soc. Hort. Sci.* 1980 105, 216–220, the disclosures of which are hereby incorporated by reference in their entirety, reported that media developed for the climbing rose Improved Blaze allowed significant growth of three miniature rose varieties but not for all hybrid tea roses. Khosh-Khui and Sink, *J. Hort. Sci.* 1982 57, 315–319 and Khosh-Khui and Sink, *Scientia Horticulturae* 1982 17, 371–376, the disclosures of which are hereby incorporated by reference in their entirety, found that plant growth regulator requirements for multiplying the *R. hybrida* cultivars, Tropicana and Bridal Pink differed considerably from those of two old world species *R. damascena* and *R. canina*.

To optimize growth conditions most studies have focused on variations in the concentrations of certain growth regulators, Hasegawa, supra. A few studies have investigated the effect of certain other inorganic or organic components. For example, Khosh-Khui and Sink, supra. investigated the effect of explant orientation, explant size and lighting on the growth of new and old world species. Bressan et al., *J. Amer. Soc. Hort. Sci.* 1982 107, 979–990, the disclosures of which are hereby incorporated by reference in their entirety, investigated the effect of bud position, temperature, hours of light per day, Murashige and Skoog ingredient concentrations, and weeks in culture between transfers.

Despite some success in developing suitable culture media and culturing processes, new and/or better media and methods, particularly for commercially significant roses, are needed. Toward this end, the present invention is directed to the development of media useful for the propagation of roses and for induction of flowering in vitro.

SUMMARY OF THE INVENTION

The present invention is directed to a method of tissue culture micropropagation of a rose plant comprising culturing a stem bearing a node in a first enclosed vessel containing a first culture medium comprising about 0.5 to about 3.0 mg/l benzyladenine, 0 to about 1.0 mg/l indole acetic acid, and 0 to about 1.0 mg/l gibberellic acid until at least one shoot is produced from said node; excising said shoot from said stem and propagating said shoot in a second enclosed vessel containing a second culture medium comprising about 0.5 to about 3.0 mg/l benzyladenine, 0 to about 1.0 mg/l indole acetic acid, and 0 to about 1.0 mg/l gibberellic acid to produce a rose plant in an enclosed vessel. In accordance with this method, the rose plant may be a flowering rose and the rose plant may be capable of growth in soil.

The present invention is also directed to a method of tissue culture micropropagation of a rose plant comprising culturing a stem bearing a node in an enclosed vessel containing culture medium comprising about 0.5 to about 3.0 mg/l benzyladenine, 0 to about 1.0 mg/l indole acetic acid, and 0 to about 1.0 mg/l gibberellic acid. The stem may be cultured until at least one shoot is produced from the node or until a rose plant is produced. A method of tissue culture micropropagation of a rose plant comprising culturing a shoot in an enclosed vessel containing culture medium comprising about 0.5 to about 3.0 mg/l benzyladenine, 0 to about 1.0 mg/l indole acetic acid, and 0 to about 1.0 mg/l gibberellic acid is also an embodiment of the present invention. The shoot may be cultured until a rose plant is produced within the enclosed vessel. In each of these methods, the rose plant may be a flowering rose, and the rose plant may be capable of growth in soil.

A culture medium for tissue culture micropropagation of a rose plant is also an embodiment of the present invention and comprises about 0.5 to about 3.0 mg/l benzyladenine, 0 to about 1.0 mg/l indole acetic acid, and 0 to about 1.0 mg/l gibberellic acid. The culture medium may further comprise a nutriative medium. Preferably the culture medium contains 3.0 mg/l benzyladenine, more preferably about 2.0 mg/l benzyladenine, and even more preferably about 1.0 mg/l benzyladenine.

The rose plant may also be subject to growth in rooting medium.

A rose plant, including a flowering rose, produced by the method is also within the scope of the present invention. The rose is preferably *Rose hybrida,* and most preferably a cultivar selected from the group consisting of Meirutral, Fairy, and Pink Miniwonder. The rose plant may be contained within the enclosed vessel. The rose plant may also be capable of growth in soil.

The present invention is also directed to a rose tissue culture comprising a rose stem bearing a node contained in an enclosed vessel containing culture medium comprising about 0.5 to about 3.0 mg/l benzyladenine, 0 to about 1.0 mg/l indole acetic acid and 0 to about 1.0 mg/l gibberellic acid. The rose stem may comprise at least one shoot, the rose tissue culture capable of producing a rose, for example, a flowering rose. A rose explant is also within the scope of the present invention. The rose explant may be selected from a rose stem bearing a node, a rose stem bearing a node and at least one shoot, and a rose shoot. The rose explant may be contained in an enclosed vessel comprising culture medium comprising about 0.5 to about 3.0 mg/l benzyladenine, 0 to about 1.0 mg/l indole acetic acid and 0 to about 1.0 mg/l gibberellic acid, and may be cultured until a rose plant is produced, a flowering rose plant, for example.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 3A shows floral bud with sepals enclosing petals. FIG. 3B exhibits floral bud with retracted petals revealing pink colored petals. FIG. 3C shows a fully opened flower. All plants have a well developed root system allowing for transplanting to soil for indoor or outdoor growth.

DETAILED DESCRIPTION OF THE INVENTION

Figure 1A:
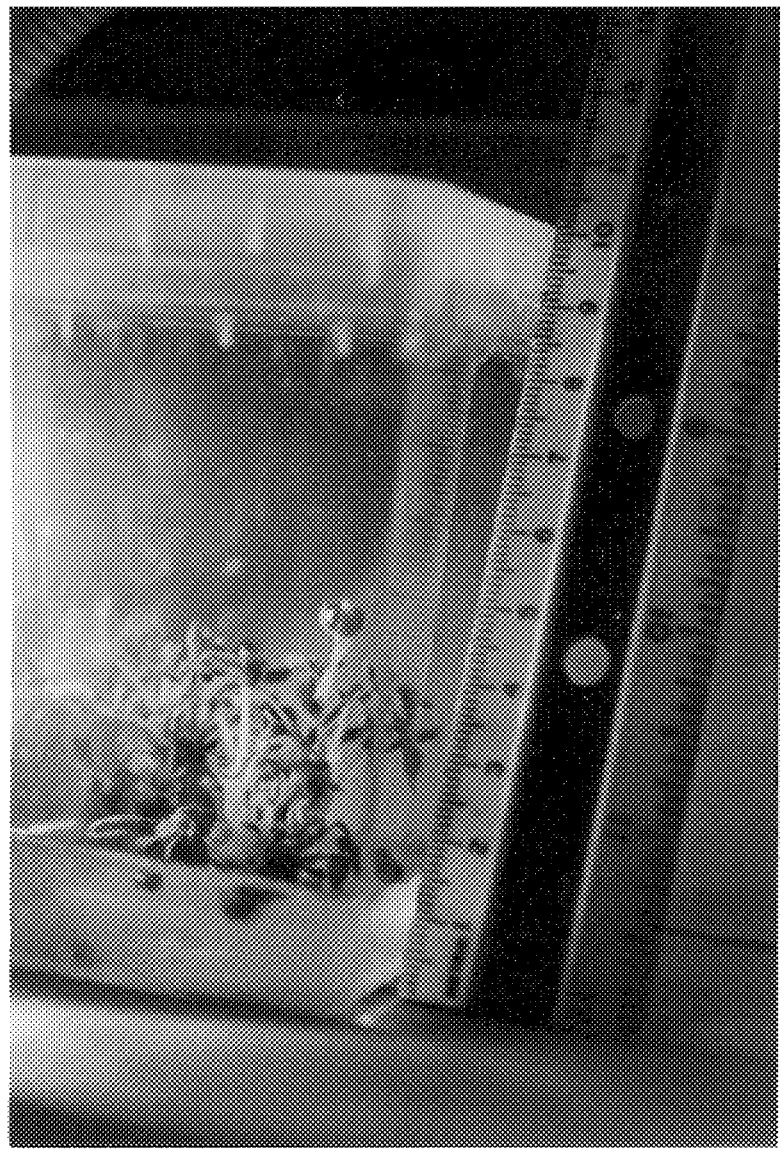
FIG. 1A depicts full view and FIG. 1B depicts a close up view of *Rosa hybrida* cv. Meirutral at an early stage of flower opening in vitro.
Figure 1B:
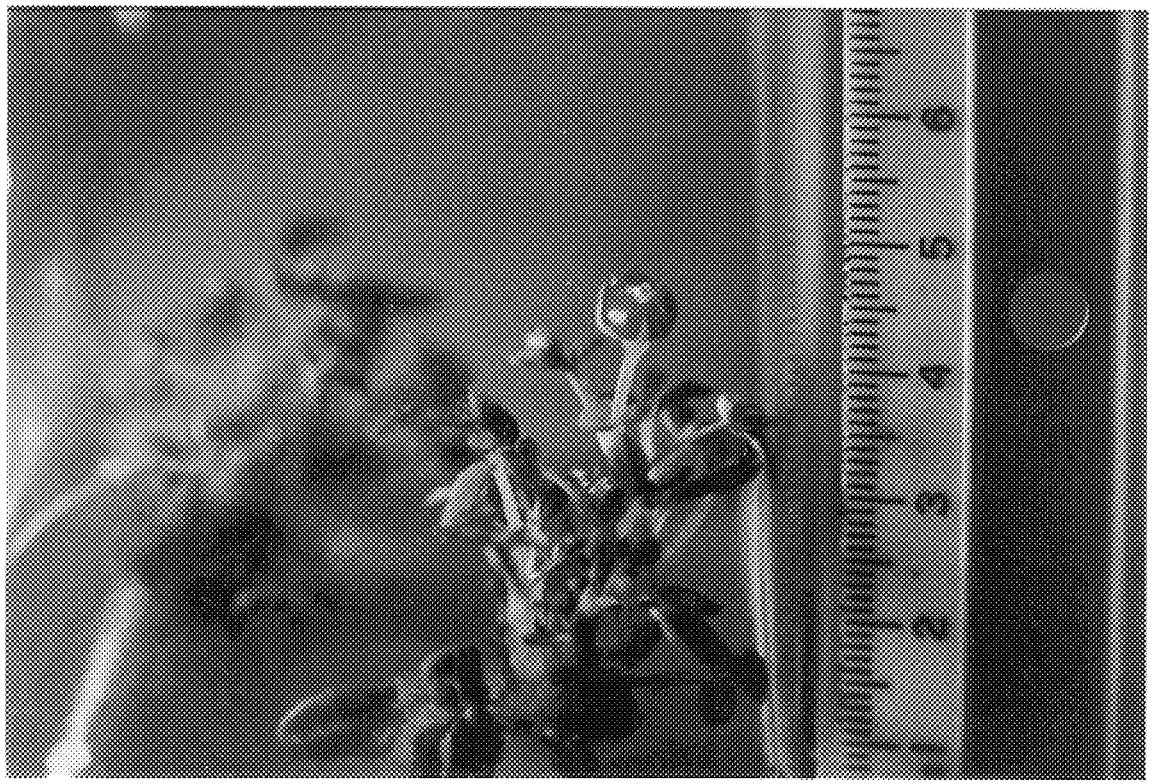
Figure 2A:
FIG. 2A shows full view and FIG. 2B shows a close up view of *Rosa hybrida* cv. Meirutral showing completely opened flower in vitro.
Figure 2B:
Figure 3A:
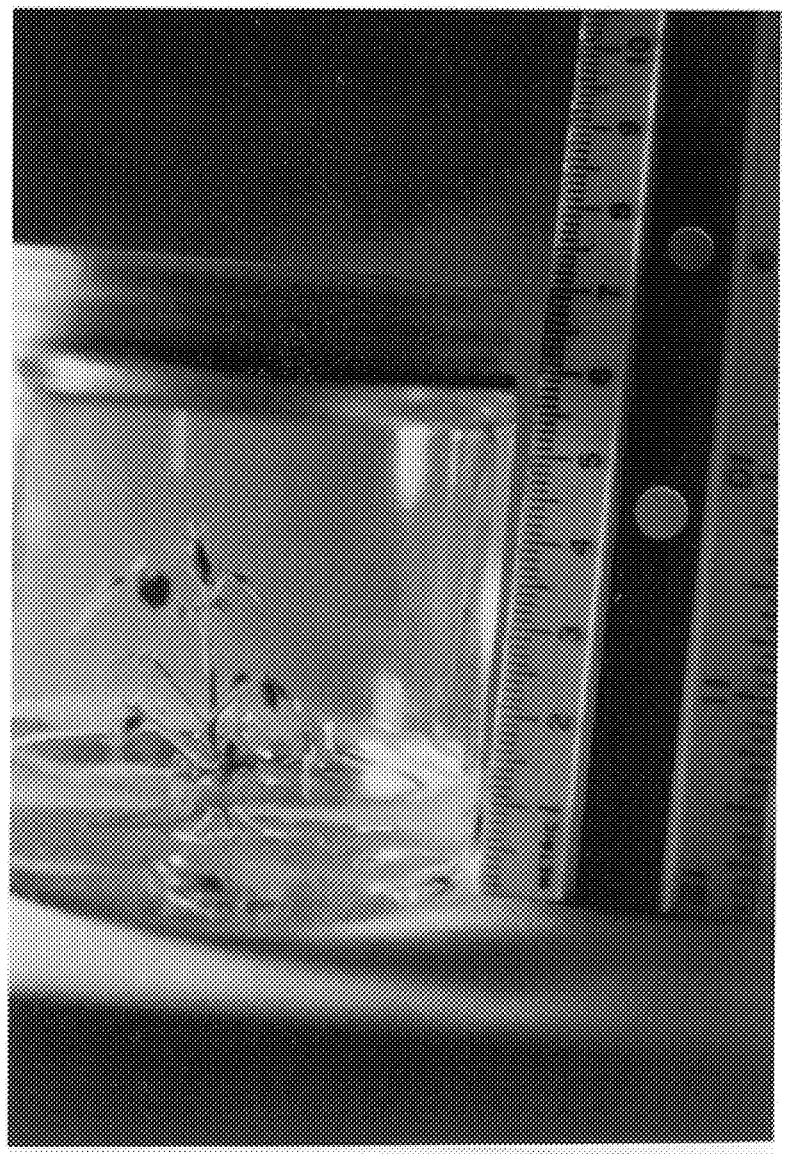
FIGS. 3A–3C depict three stages of flower development of *Rosa hybrida* cv. Pink Miniwonder in vitro.
Figure 3B:
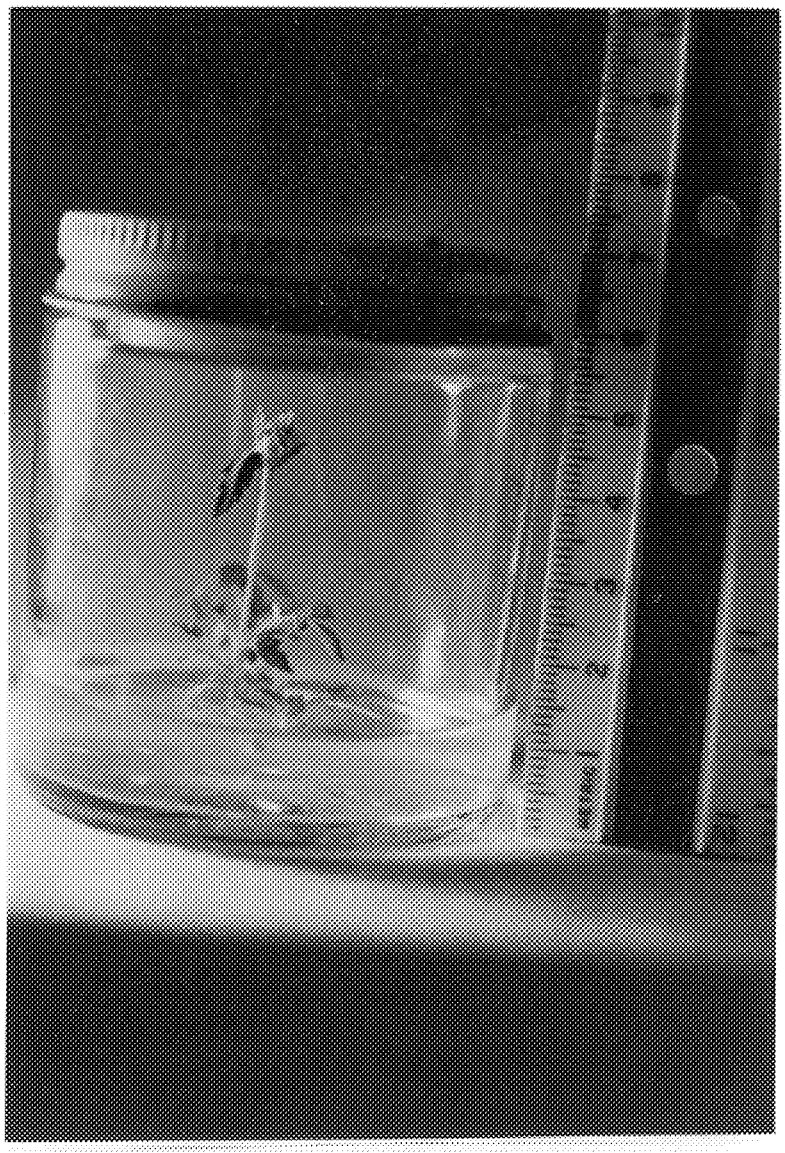
Figure 3C:

The present invention is directed, inter alia, to a flowering rose plant which may remain in culture without feeding or watering for a period of time which permits the plant to continue to be sustained. Once the rose flowers in the enclosed vessel, it typically may be maintained for at least about three (3) weeks, more preferably for at least about four (4), more preferably for at least about six (6), even more preferably for at least about eight (8) weeks, and most preferably for at least about twelve (12) weeks. Alternatively, the flowering rose plant may be removed from the enclosed vessel and be transferred to soil for use as an indoor or outdoor plant.

In accordance with the present invention, micropropagation is defined as replicating a parent plant such that the resulting plants are identical to the parent plant. Micropropagation is carried out with rose plant tissue (a rose explant) obtained from a rose plant. In accordance with the present invention, a rose plant is defined herein as a shoot having no roots (wherein said shoot may be induced to root), and a shoot having a root system. Each type of rose plant, with or without root system may bear flowers in accordance with the methods of the present invention. The explant may be mature or immature, preferably immature. The explant may be at least one cell from a rose plant, a rose stem, preferably a rose stem bearing at least one node, a rose stem bearing a node and at least one shoot, a rose shoot, and a shoot having roots. A rose stem is a cutting of a rose plant from the stem of the plant. A rose stem may be cut from any where along the length of the rose plant stem and generally is of a length of about one quarter of an inch (¼) to about three (3) inches, preferably about one inch to about one and one half inches. It has been found that variation in explant source may effect the performance of the explant in the enclosed vessel, such that rose stems obtained from the area of the stem closer to the shoot tip tends to perform more favorably in the methods of the present invention. A node is an area on a stem which develops into a shoot. Similarly, a rose shoot generally is of a length of about one quarter of an inch (¼) to about six (6) inches, preferably about one inch to about one and one half inches.

The present invention is directed to a method of tissue culture micropropagation of a rose plant comprising culturing a stem bearing a node in a first enclosed vessel containing a first culture medium comprising about 0.5 to about 3.0 mg/l benzyladenine, 0 to about 1.0 mg/l indole acetic acid and 0 to about 1.0 mg/l gibberellic acid until at least one shoot is produced from the node; excising the shoot from the stem and propagating the shoot in a second enclosed vessel containing a second culture medium comprising about 0.5 to about 3.0 mg/l benzyladenine, 0 to about 1.0 mg/l indole acetic acid and 0 to about 1.0 mg/l gibberellic acid to produce a flowering rose plant in an enclosed vessel capable of being further propagated in vitro and/or transferred to soil.

The time needed to culture the stem to a flowering rose plant in vitro, is a time effective to produce a flowering rose plant in accordance with the methods of the present invention, typically about three (3) to about six (6) weeks, preferably about four (4) weeks. The second enclosed vessel may be the same as the first vessel, or a different vessel.

The present invention is also directed to each individual step of the two steps of the method of tissue culture micropropagation set forth above. A rose plant is propagated by culturing a stem bearing at least one node in an enclosed vessel comprising the aforementioned culture medium. The stem may be cultured until at least one shoot is produced from the node. Alternatively the stem may be cultured for a time effective to produce a rose plant, typically about three (3) to about six (6) weeks, preferably about four (4) weeks. The shoot produced from the node of the above-identified method, or a shoot obtained as an explant from a rose plant, may be used in a method of tissue culture micropropagation comprising culturing the shoot in an enclosed vessel comprising the aforementioned culture medium. The shoot may be cultured for a time effective to produce a rose plant, typically about three (3) to about six (6) weeks, preferably about four (4) weeks. The rose plant may be produced within the enclosed vessel and may be a flowering rose. Further the rose plant may be capable of growth in soil such that the rose plant may be potted for indoor or outside use.

Preferably, the method present invention is carried out a medium comprising 3 mg/l benzyladenine, more preferably 2.0 mg/l benzyladenine, and even more preferably 1.0 mg/l benzyladenine while the concentration of indole acetic acid is about 0.3 mg/l and the concentration of gibberellic acid is about 0.01 to about 0.5 mg/l, more preferably about 0.1 mg/l. The concentration of benzyladenine is at least about 0.5 mg/l, while indole acetic acid and gibberellic acid may not be included, however, are preferably included at 0 to about 1.0 mg/l each.

Benzyladenine, a cytokine also known as 6-benzylaminopurine, may be substituted with another natural or synthetic cytokine selected from the group consisting of 6-benzylaminopurine riboside; 1-phenyl-3-(1,2,3-thiadiazol-5-yl) urea; 6-(γ-γ-dimethylallylamino)purine; DL-Dihydrozeatin; t-zeatin riboside; zeatin; N-(2-Chloro-4-pyridyl)-N'-phenylurea; N-benzyl-9-(2-tetrahydropyranyl) adenine; kinetin; kinetin riboside; and isopentyladenosine, wherein the cytokine may be used alone or in combination with one or more cytokine. Indole acetic acid, an auxin, may be substituted with another natural or synthetic auxin selected from the group consisting of naphthaleneacetic acid (NAA), indole butyric acid (IBA), picloram, dicamba, and 2,4-dichlorophenoxy acetic acid (2,4-D), at a concentration of about 0.03 to about 0.3 mg/l, wherein the auxin may be used alone or in combination with one or more auxin. Giberellins include various forms of gibberellic acid, such as and not limited to GA3, GA4, GA7, and iso-gibberellin A7.

As those skilled in the art would recognize, the general nutritional and growth requirements of tissue cultured plant cells must be satisfied. The general nutritional, hormonal, and growth requirements of plant cells are well known, and a number of conventional culture media and growth protocols have been developed which satisfy these needs (hereinafter referred to herein as nutriative medium). See, e.g., MSG medium (Becwar, M. R., et al., "Development and Characterization of In Vitro Embryogenic Systems in Conifers", in *Somatic Cell Genetics of Woody Plants*, ed. Ahuja, M. R., Kluwer Academic Publishing, Dordrecht, The Netherlands (1988)), Shenk-Hildebrandt (SH) culture medium (Shenk et al., *Can. J. Bot.*, Vol. 50, pp. 199–204 (1972)), Murashige-Skoog (M-S) basal media (Murashige et al., *Physiol. Plant.*, Vol. 15, pp. 473–97 (1962)), and White's medium (White, The Cultivation of Animal and Plant Cells, 2nd ed., Ronald Press Co., New York (1963)). A comprehensive list of plant culture media and culture protocol are found in Huang et al., Plant Tissue Culture Media, TCA Manual, Vol. 3, pp. 539–48, Tissue Culture Association, Rockville, Md. (1977). The disclosures of each of these references are incorporated herein by reference in their entirety. The foregoing culture media and culture protocol, as well as others known to those skilled in the art, can be employed in conjunction with the methods and medium of the present invention. In accordance with the invention, however, sucrose, or other carbon sources including and not limited to glucose, sorbitol, mannitol, fructose, and galactose, must necessarily be present, and indoleacetic acid preferably present, each in the amounts set forth herein, for the efficient and effective production of flowering rose plants from the rose explant.

Within this general framework, and in addition to the aforementioned components benzyladenine, indole acetic acid and gibberellic acid, the culture medium of the present invention may further comprise a nutriative medium. Preferably the medium is Murashige and Skoog (MS) medium. MS medium comprises salts such as and not limited to at least about 400 mg/l, preferably about 1650 mg/l ammonium nitrate, at least about 1 mg/l, preferably about 6.2 mg/l boric acid, at least about 75 mg/l, preferably about 332 mg/l, more preferably 332.2 mg/l calcium chloride (anhydrous), at least about 0.005 mg/l, preferably about 0.025 mg/l cobalt chloride.6H$_2$O, at least about 0.005, preferably about 0.025 mg/l cupric sulfate.5H$_2$O, at least about 3 mg/l, preferably about 37 mg/l, more preferably about 37.26 mg/l sodium ethylene diamine tetraacetic acid (Na$_2$.EDTA), at least about 6 mg/l, preferably about 27–28 mg/l, more preferably about 27.8 mg/l ferrous sulfate.7H$_2$O, at least about 45 mg/l, preferably about 180 mg/l, more preferably about 180.7 mg/l magnesium sulfate, at least about 4 mg/l, preferably about 16–17 mg/l, more preferably about 16.9 mg/l manganese sulfate.H$_2$O, at least about 0.05 mg/l, preferably about 0.25 mg/l molybdic acid (sodium salt).2H$_2$O, at least about 0.2 mg/l, preferably about 0.83 mg/l potassium iodide, at least about 500 mg/l, preferably about 1900 mg/l potassium nitrate, about 170 mg/l potassium phosphate (monobasic), and at least about 2 mg/l, preferably about 8.6 mg/l zinc sulfate.7H$_2$O. The culture medium may further comprise Gamborg's B5 vitamins comprising about 10 to about 200 mg/l, preferably about 100 mg/l myo-inositol, at least about 0.5 to about 5 mg/l, preferably about 1.0 mg/l nicotinic acid, at least about 0.5 to about 5.0 mg/l, preferably about 1.0 mg/l pyridoxine.HCl, and at least about 5 to about 20 mg/l, preferably about 10 mg/l thiamine.HCl. These vitamins may also be used singularly or in various combinations of two or more vitamins. Further, other vitamins and vitamin combinations may be substituted therefor.

The preferred composition of the culture medium of the present invention comprises MS medium containing Gamborg's B5 vitamins, at least about 0.5 mg/l, preferably 2 mg/l glycine, at least about 10 mg/l, preferably 50 mg/l ascorbic acid, at least about 10 mg/l, preferably 50 mg/l citric acid, at least about 10 g/l, preferably about 30 g/l sucrose, and at least about 1.5 g/l, preferably about 3 g/l PHYTAGEL™. This medium is added to about 0.5 to about 3.0 mg/l benzyladenine, preferably 3 mg/l, more preferably about 2.0 mg/l, and even more preferably about 1.0 mg/l; 0 to about 1.0 mg/l, preferably 0.3 mg/l indole acetic acid and 0 to about 1.0 mg/l, preferably 0.1 mg/l gibberellic acid.

The minimal requirements for shoot growth include the aforementioned basic salts, such as those of MS medium, about 0.1 to about 0.5 mg/l cytokine, such as and not limited to benzyladenine, and about 5 to about 10 g/l of a carbon source such as and not limited to sucrose.

The media may be modified such that hormonal constituents are provided for specific varieties of plants. Nutrient levels may be modified in the basal media to induce flowering. For example, Murashige and Skoog (MS) medium, which provides the general nutritional and growth requirements of tissue culture plant cells, may be substituted with other conventional culture or growth medium such as and not limited to those disclosed by Becwar, M. R., et al., "Development and Characterization of In Vitro Embryogenic Systems in Conifers", in *Somatic Cell Genetics of Woody Plants*, ed. Ahuja, M. R., Kluwer Academic Publishing, Dordrecht, The Netherlands (1988), Shenk-Hildebrandt (SH) culture medium Shenk et al., *Can. J. Bot.*, Vol. 50, pp. 199–204 (1972), White, The Cultivation of Animal and Plant Cells, 2nd ed., Ronald Press Co., New York (1963) and Gamborg et al., *Exp. Cell Res.* 1968, 50, 151–158, the disclosure of each reference cited herein is incorporated herein by reference in its entirety.

Within these general parameters, the precise amount of each component to be employed will depend upon various factors, such as the type of rose to be cultured, as will be readily apparent to those skilled in the art. Typically, the compounds are initially employed at the lower levels, and the amounts increased as necessary to achieve the desired effect. For example, a preferred composition of MS medium containing Gamborg's B5 vitamins, about 0.5 to about 5.0 mg/l glycine, about 10 to about 100 mg/l ascorbic acid, about 10 to about 100 mg/l citric acid, about 10 to about 30 g/l, preferably 30 g/l sucrose, and about 1.5 to about 3.0 g/l, preferably 3 g/l Phytagel™ may be used in the present invention.

Glycine may be used at concentrations of about 0.5 to about 5.0 mg/l, and may be substituted by other amino acids, such as and not limited to alanine and proline; mixture of naturally occurring amino acids, at a similar concentration range; crude mixtures such as casein hydrolysate at concentration of about 0.5 to about 10 g/l; coconut water at a concentration of between about 1 to about 20 g/l. Ascorbic acid and citric acid may be used in the range of about 10 to about 100 mg/l. Gibberellic acid may be used in the range of about 0.01 to about 0.5 mg/l. Any suitable gelling agent such as and not limited to PHYTAGEL™ comprising gellan gum, GEL-RITE™ comprising gellan gum; AGARGEL™ comprising gellan gum; agar such as and not limited to agar types A, E, and M, High Gel Strength, Purified, Bacteriological Flake, and Washed; AGARGEL™ a blend of agar and PHYTAGEL™; agarose, such as and not limited to Type VII; alginic acid; carrageenan; transfergel or hydroxyethylcellulose; and the like. GEL-RITE™ is used at half the concentration recommended by the present invention for the other gelling agents. One or more of the ingredients of the culture medium may be omitted, without substitution therefor, including and not limited to gibberellic acid, glycine, ascorbic acid, citric acid, and/or indole acetic acid.

In addition to alternative medium compositions, success of the micropropagation technique may be enhanced by additional conditions as well. Such conditions will be readily apparent to those skilled in the art and include choosing donor tissues for culture initiation which come from plants of appropriate genotype as well as physiological and development states, variation of explant source and the plant variety, and physical environment in which the cultures are grown. For example, gaseous conditions may be modified within the enclosed vessel to allow ethylene and air to be exchanged. Temperature and light conditions may be varied to provide for an improved rose plant contained in an enclosed vessel.

Further to the methods and culture medium set forth above, the present invention is also directed to propagating a shoot in a third enclosed vessel containing a rooting medium comprising nutriative medium. The nutriative medium contained in the rooting medium is preferably MS medium. However, any of the aforementioned nutriative media may be useful in the rooting medium as well. In addition to nutriative medium, the rooting medium also comprises about 1 to about 5 mg/l, preferably about 2.0 mg/l glycine, about 50 to about 150 mg/l, preferably about 100 mg/l myo-inositol, about 0.1 to about 1.0 mg/l, preferably about 0.5 mg/l nicotinic acid, about 0.1 to about 1.0 mg/l, preferably about 0.5 mg/l pyridoxine.HCl, about 0.01 to about 0.2 mg/l, preferably about 0.1 mg/l thiamine.HCl, about 10 to about 50 g/l, preferably about 30 g/l sucrose, and optionally containing about 1 to about 5 g/l, preferably about 3 g/l gelling agent, about 0.05 to about 1 mg/l, preferably about 1 mg/l, more preferably about 0.05 mg/l indole butyric acid. The gelling agent may be any of the aforementioned gelling agents, as well as water, sterilized soil, cellulose foam or fiber rooting materials such as and not limited to Sorbarod™. The rooting medium may even further comprise about 0.01 to about 0.2 mg/l, preferably about 0.1 mg/l naphthaleneacetic acid. At a minimum, rooting medium may simply comprise ¼×MS salts. In addition about 0.1 mg/l of an auxin such as and not limited to indole acetic acid may be added to the ¼×MS salts. Preferred rooting media of the present invention include and are not limited to the following compositions: 0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose and 3.0 g/l PHYTAGEL™, and 1 mg/l IBA; 0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL™, and 1 mg/l IBA; 0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL, 0.05 mg/l IBA, and 0.1 mg/l NAA; 0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL™, 0.05 mg/l IBA and 0.1 mg/l NAA; 0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, and 3.0 g/l PHYTAGEL™; and 0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose and 3.0 g/l PHYTAGEL™.

The rose explant, per se, is an embodiment of the present invention. The rose explant may be contained in an enclosed vessel comprising the aforementioned culture medium, and may be cultured until a rose plant is produced, a flowering rose plant, for example. The explants may be obtained from a plant, such as and not limited to the genus Rosa, including and not limited to the hybrid rose *Rosa hybrida,* such as and not limited to the cultivars Meirutral (Red Sun Blaze™), Fairy, Pink Miniwonder, Mr. Lincoln, Royalty, Chrysler Imperial, Frisco, Sonia, Peach and the like; *Rosa damascena, Rosa multiflora,* and *Rosa gallica,* and the like.

The tissue culture techniques of the present invention comprise culturing a rose explant in an enclosed vessel such as and not limited to a petri dish, a test tube, a Magenta™ box, an eppendorf tube, a baby food jar, a canning jar, and any other enclosed container capable of supporting the growth of the rose plant of the present invention in accordance with the methods of the present invention. The enclosed vessel comprises a culture medium comprising about 0.5 to about 3.0 mg/l benzyladenine, 0 to about 1.0 mg/l indole acetic acid, and 0 to about 1.0 mg/l gibberellic acid.

A rose, including a flowering rose, produced by the methods of the present invention, is also within the scope of the present invention. The rose may be *Rose hybrida,* and a cultivar selected from, and not limited to, the group consisting of Meirutral (Red Sun Blaze™), Fairy, and Pink Miniwonder. The rose plant may be contained within the enclosed vessel.

Rose tissue culture, per se, is within the scope of the present invention. A rose tissue culture comprising an explant, such as and not limited to a rose stem bearing at least one node, a rose stem bearing a node and at least one shoot, or a rose shoot, contained in an enclosed vessel containing culture medium comprising about 0.5 to about 3.0 mg/l benzyladenine, 0 to about 1.0 mg/l indole acetic acid, and 0 to about 1.0 mg/l gibberellic acid, is also an embodiment of the present invention. The rose tissue culture is capable of producing a rose, such as a flowering rose, and may be transferred to soil, for indoor or outside use.

The rose in an enclosed vessel may be used to screen new cultivars for flower color and form. For example, plants may be subjected to mutational treatment during tissue culture of rose callus, explants or axillary bud. Mutated rose plants may then be grown in the culture of the present invention and screened for those with altered flower color, form, disease resistance, growth vigor, cold and heat sensitivity, and any other valuable trait. In addition, the present invention also permits performing cross pollination of rose plants in culture. For example, since flowers contain visibly developed male and female organs, such flowers may be pollinated with pollen derived from the same flower or from a plant of any other source.

In the preferred method of the invention, rose stems are selected and excised in sections less than about 6 inches in length. Terminal buds and all leaves are removed from stems and each stem is cut into segments containing at least one node. Excised stem segments are then washed with warm soap and water and rinsed with tap water. Stem segments are then surface sterilized which may be carried out in a laminar flow hood. Stem segments are placed in ethanol and rinsed in sterile, distilled water and then swirled in sterile, distilled water. Stem segments may then be placed in a shaking bleach solution. Finally, stem segments are rinsed three times with sterile, distilled water, for about 3 to about 5 minutes/rinse. Stem segments are then cultured by placing 2 to 3 segments in a sterile, disposable petri dish. The bleached ends of stem pieces are removed with a scalpel and the basal end (the end closest to the root in the parent plant) of one stem segment is placed, with node, approximately ¼ inch into culture medium, into a test tube containing about 5 to about 50 ml, preferably about 20 ml of such medium. Cultures are grown under lights (about 16 hours daylength) on growth rack in culture room at about 24°–25° C.

After about 25 days, nodes typically give rise to multiple new shoots. Each shoot is separately excised and transferred to fresh media. Approximately 17 days after this transfer, about 10% of the new shoots may bear a single floral bud about 3–5 mm in length. These buds then proceed to open.

The present invention is further described in the following examples. These examples are not to be construed as limiting the scope of the appended claims.

EXAMPLES

Example 1

A plant designated *Rosa hybrida* cv. Meirutral (U.S. Plant Patent 7,021, the disclosures of which are hereby incorporated by reference in their entirety) was obtained from the greenhouses of Conard-Pyle Co., West Chester, Pa. About one month later, young, healthy stems were selected and excised as sections approximately 4–5 inches in length. Terminal buds and all leaves were removed from stems and each stem was cut into segments containing at least one node, 1 inch to 1½ inches in length. Excised stem segments were then washed with warm soap and water and rinsed well with tap water.

Stem segments were surface sterilized in a laminar flow hood by the following procedure. Stem segments were placed in 70% ethanol for about 2 minutes then rinsed in sterile, distilled water followed by swirling in sterile, distilled water for about 3–5 minutes. Stem segments were then placed in a 20% bleach solution (Chlorox, Proctor & Gamble, Cincinnati, Ohio) containing one drop (ca. 100 $\mu$l) of detergent for 20 minutes with shaking. Finally, stem segments were rinsed three times with sterile, distilled water (3–5 minutes/rinse.)

Stem segments were cultured by the following procedure. Segments (2–3 at a time) were placed in a sterile, disposable petri dish. The bleached ends of stem pieces were removed with a scalpel. The basal end of one stem segment was placed, with node, approximately ¼ inch into culture medium, into a test tube containing about 20 ml of such medium. Each culture was labelled with experiment number, stem segment number and date. Cultures were grown under lights (16 hours daylength) on growth rack in a culture room (24°–25° C.). The effects of three different media were tested. MS basal media (Murashige 1962, the disclosures of which hereby incorporated by reference in their entirety) containing Gamborg's B5 vitamins was supplemented with glycine 2.0 mg/l, 50 mg/l ascorbic acid and 50 mg/l citric acid, sucrose (30.0 g/l) PHYTAGEL™ (3.0 g/l) and adjusted to pH 5.7. The three variations tested further contained the growth regulators, benzyladenine (BA), indole acetic acid (IAA), and gibberellic acid (GA3). The three media (BIG-4, BIG-5, and BIG-6) tested varied in their concentration of BA. BIG-4 contained 3 mg/l BA, 0.3 mg/l IAA and 0.1 mg/l GA3; BIG-5 contained 2 mg/l BA, 0.3 mg/l IAA, 0.1 mg/l GA3; BIG-6 contained 1 mg/l BA, 0.3 mg/l IAA and 0.1 mg/l GA3.

After 25 days, most nodes had given rise to multiple (2–4) new shoots. Each shoot was separately excised and transferred to fresh media (BIG 4, 5 or 6 respectively), see Table 1, row 2. Approximately 17 days after this transfer, approximately 10% of the new shoots were seen to bear a single floral bud about 3–5 mm in length, see Table 1, row 5. In most cases, these buds proceeded to open. The first floral buds appeared on the largest shoots and produced flowers with small but otherwise normal looking petals, sepals, stamens and ovaries.

Individual plants were subsequently divided by cutting between nodes and subcultured on the same medium as the previous culture. At 47 days (from the time of the time the original culture was started) flowers were observed on 2 out of 38, 5 out of 33, and 6 out of 30 plants grown on BIG-4, BIG-5, and BIG-6, respectively.

On the 76th day, plants were again divided by cutting between nodes and subcultured on the same medium as the previous culture. At day 88, 4 out of 46, 3 out of 26, and 6 out of 40 plants bore flowers in BIG-4, BIG-5, and BIG-6 respectively.

Since the percentage of flower buds increased with decreasing BA concentration, it appears that lower concentrations of BA induce optimal flower formation.

In a similar experiment, *R. hybrida* cv. The Fairy, formed flower buds which have opened. The ability to induce flower formation in culture appears to rely on a specific combination of media and genotype. In this case, *R. hybrida* cv. Meirutral is particularly suited to the formation of flowers in vitro using the media tested.

TABLE 1

|  |  | BIG-4 | BIG-5 | BIG-6 |
|---|---|---|---|---|
| Culture 1 | NODES 102-0 10 days | 17 | 22 | 14 |
| Culture 2 | SHOOTS 102-1 25 days | 23 | 25 | 17 |
| Culture 3 | SHOOTS 102-2 45 days | 38 | 33 | 30 |
| Culture 4 | SHOOTS 102-3 76 DAYS | 46 | 26 | 40 |
| Culture 2 | FLOWERS 42 days | 2/23 | 3/25 | 2/17 |
| Culture 3 | FLOWERS 47 days | 2/38 | 5/33 | 6/30 |
| Culture 4 | FLOWERS 88 days | 4/46 | 3/26 | 6/40 |
| Culture 2 | % FLOWERS 42 days | 8.7 | 12.0 | 11.8 |
| Culture 3 | % FLOWERS 47 days | 5.3 | 15.2 | 20.0 |
| Culture 4 | % FLOWERS 88 days | 8.7 | 11.54 | 15 |

Example 2

The following procedure was used to produce a plant designated *Rosa Hybrida* cv. Pink Miniwonder that flowered in vitro.

Stem segments were surface sterilized in a laminar flow hood by the following procedure. Stem segments were placed in 70% ethanol for 2 minutes then rinsed in sterile, distilled water followed by swirling in sterile, distilled water for 3–5 minutes. Stem segments were then placed in a 20% chlorox solution containing one drop (ca. 100 μl) of detergent for 20 minutes with shaking. Finally, stem segments were rinsed 3 times with sterile, distilled water (3–5 minutes/rinse).

Stem segments were cultured by the following procedure. Segments (2–3 at a time) were placed in a sterile, disposable petri dish. The bleached ends of stem pieces were removed with a scalpel. The basal end of one stem segment was placed, with node, approximately ¼-inch into culture medium, into a test-tube containing 20 ml of such medium. Each culture was labelled with experiment number, stem segment number and date. Cultures under lights (16 hour day length) on growth rack in culture room (24°–25° C.).

The effects of two different media were tested. The first media termed BIG-3 contained MS basal media (Murashige and Skoog, *Physiologia Plantarum* 1962, 15, 473–497, the disclosures of which are incorporated herein by reference in their entirety) containing Gamborg's B5 vitamins, Gamborg et al., *Exp. Cell Res.* 1968, 50, 151–158, the disclosures of which are incorporated herein by reference in their entirety. The media was supplemented with glycine 2.0 mg/l, sucrose (30.0 g/l), PHYTAGEL™ (3.0 g/l), 3 mg/l BA, 0.3 mg/l IAA, and 0.1 mg/l GA3, and adjusted to pH 5.7. The second media termed BIG-4 in addition to the above contained 50 mg/l ascorbic acid and 50 mg/l citric acid.

Plants were transferred every 2 to 4 weeks into new medium, identical to the medium from which the plant was transferred, for a total of 9 transfers for about 4 months before being transferred to four different kinds of rooting media.

Rooting I:

0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose and 3.0 g/l PHYTAGEL™, and 1 mg/l IBA.

Rooting IA:

0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL™, and 1 mg/l IBA.

Rooting II:

0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL, 0.05 mg/l IBA, and 0.1 mg/l NAA.

Rooting IIA:

0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, 3.0 g/l PHYTAGEL™, 0.05 mg/l IBA and 0.1 mg/l NAA.

Rooting 4:

0.25×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose, and 3.0 g/l PHYTAGEL™.

Rooting 5:

0.5×MS salts, 2 mg/l glycine, 100 mg/l myo-inositol, 0.5 mg/l nicotinic acid, 0.5 mg/l pyridoxine.HCl, 0.1 mg/l thiamine.HCl, 30 g/l sucrose and 3.0 g/l PHYTAGEL™.

After about three weeks, roots had developed in each type of rooting media. In addition, in rooting media I and IIA about 20% of the plants had developed flower buds. The induction of flowering in this case is due to the absence of BA in rooting media and/or the presence of auxins that might act to enhance ethylene biosynthesis and thereby stimulate flower production. In addition, the tendency of plants to flower may also be enhanced by the reduced MS salts concentrations. That is, flowering of rose plants in vivo is known to be enhanced by reduced nutrients (fertilizers).

Various modifications of the invention in addition to those shown and described herein will be apparent to those skilled in the art from the foregoing description. Such modifications are also intended to fall within the scope of the appended claims.

What is claimed is:

1. A method of tissue culture micropropagation of a rose plant comprising culturing a stem bearing a node in a first enclosed vessel containing a first culture medium comprising about 0.5 to about 3.0 mg/l of a cytokine, 0 to about 1.0 mg/l of an auxin, and 0 to about 1.0 mg/l of a gibberellin until at least one shoot is produced from said node; excising said shoot from said stem and propagating said shoot in a second enclosed vessel containing a second culture medium comprising about 0.5 to about 3.0 mg/l of a cytokine, 0 to about 1.0 mg/l of an auxin, and 0 to about 1.0 mg/l gibberellic acid to produce a flowering rose plant in an enclosed vessel.

2. The method of claim 1 wherein said cytokine is benzyladenine, said auxin is indole acetic acid, and said gibberellin is gibberellic acid.

3. The method of claim 2 wherein said first and said second culture media comprise about 1.0 mg/l benzyladenine, about 0.3 mg/l indole acetic acid, and about 0.1 mg/l gibberellic acid.

4. The method of claim 2 wherein said first and said second culture media comprise about 2.0 mg/l benzyladenine, about 0.3 mg/l indole acetic acid, and about 0.1 mg/l gibberellic acid.

5. The method of claim 2 wherein said first and said second culture media comprise about 3.0 mg/l benzyladenine, about 0.3 mg/l indole acetic acid, and about 0.1 mg/l gibberellic acid.

6. The method of claim 2 wherein said first and said second culture media further comprises a nutriative medium.

7. The method of claim 6 wherein said nutriative medium comprises MS medium in combination with Gamborg's B5 vitamins.

8. The method of 7 wherein said culture media comprises about 0.5 to about 3.0 mg/l of benzyladenine, about 0.3 mg/l of indole acetic acid, and about 0.1 mg/l gibberellic acid.

9. The method of 7 wherein said culture media comprises about 1.0 mg/l benzyladenine.

10. The method of 7 wherein said culture media comprises about 2.0 mg/l benzyladenine.

11. The method of 7 wherein said culture media comprises about 3.0 mg/l benzyladenine.

12. The method of claim 2 wherein said rose plant is *Rosa hybrida*.

13. The method of claim 12 wherein said *Rosa hybrida* is selected from the cultivars consisting of Meirutral, Fairy, and Pink Miniwonder.

14. The method of claim 2 wherein said rose plant is capable of being transferred to soil.

15. The method of claim 2 further comprising removing said rose plant from an enclosed vessel.

16. The method of claim 15 further comprising planting said rose plant in soil.

17. The method of claim 2 wherein the step of excising said shoot from said stem and propagating said shoot in a second enclosed vessel containing a second culture medium comprising about 0.5 to about 3.0 mg/l benzyladenine, 0 to about 1.0 mg/l indole acetic acid, and 0 to about 1.0 mg/l gibberellic acid to produce a rose plant in an enclosed vessel is repeated more than one time.

18. The method of claim 2 further comprising propagating said shoot in a third enclosed vessel containing a rooting medium.

19. The method of claim 18 wherein said rooting medium comprises MS medium, about 1 to about 5 mg/l glycine, about 50 to about 150 mg/l myo-inositol, about 0.1 to about 1.0 mg/l nicotinic acid, about 0.1 to about 1.0 mg/l pyridoxine.HCl, about 0.01 to about 0.2 mg/l thiamine.HCl, about 10 to about 50 g/l sucrose, about 1 to about 5 g/l gelling agent, and optionally containing about 0.05 to about 1 mg/l indole butyric acid.

20. The method of claim 19 further comprising about 0.01 to about 0.2 mg/l naphthaleneacetic acid.

21. The method of claim 20 further comprising propagating said shoot in a third enclosed vessel containing a rooting medium.

22. The method of claim 21 wherein said rooting medium comprises MS medium, about 1 to about 5 mg/l glycine, about 50 to about 150 mg/l myo-inositol, about 0.1 to about 1.0 mg/l nicotinic acid, about 0.1 to about 1.0 mg/l pyridoxine.HCl, about 0.01 to about 0.2 mg/l thiamine.HCl, about 10 to about 50 g/l sucrose, about 1 to about 5 g/l gelling agent, and optionally containing about 0.05 to about 1 mg/l indole butyric acid.

23. The method of claim 22 further comprising about 0.01 to about 0.2 mg/l naphthaleneacetic acid.

24. The method of claim 1 wherein said first culture medium comprises at least about 0.5 mg/l glycine, at least about 10 mg/l ascorbic acid, and at least about 10 mg/l citric acid and said second culture medium comprises at least about 0.5 mg/l glycine, at least about 10 mg/l ascorbic acid, and at least about 10 mg/l citric acid.

25. A method of tissue culture micropropagation of a rose plant comprising culturing a stem bearing a node in an enclosed vessel containing culture medium comprising about 0.5 to about 3.0 mg/l benzyladenine, 0 to about 1.0 mg/l indole acetic acid, and 0 to about 1.0 mg/l gibberellic acid, wherein said stem is cultured until at least one shoot is produced from said node, said shoot produced from said node capable of producing a rose plant bearing a flower, or until a flowering rose plant is produced in said enclosed vessel.

26. The method of claim 25 wherein said rose plant s capable of being transferred to soil.

27. The method of claim 25 further comprising removing said rose plant from an enclosed vessel.

28. The method of claim 27 further comprising planting said rose plant in soil.

29. A method of tissue culture micropropagation of a rose plant comprising culturing a shoot in an enclosed vessel containing culture medium comprising about 0.5 to about 3.0 mg/l benzyladenine, 0 to about 1.0 mg/l indole acetic acid, and 0 to about 1.0 mg/l gibberellic acid, wherein said shoot is cultured until a flowering rose plant is produced in said enclosed vessel.

30. The method of claim 29 wherein said rose plant is capable of being transferred to soil.

31. The method of claim 30 further comprising removing said rose plant from an enclosed vessel.

32. The method of claim 31 further comprising planting said rose plant in soil.

33. A culture medium for tissue culture micropropagation of a rose plant comprising about 0.5 to about 3.0 mg/l benzyladenine, 0 to about 1.0 mg/l indole acetic acid, and 0 to about 1.0 mg/l gibberellic acid.

34. The culture medium of claim 33 further comprising a nutriative medium.

35. The culture medium of claim 34 wherein said nutriative medium comprises MS medium in combination with Gamborg's B5 vitamins.

36. The culture medium of claim 35 comprising about 0.5 to about 3.0 mg/l of benzyladenine, about 0.3 mg/l of indole acetic acid, and about 0.1 mg/l gibberellic acid.

37. The culture medium of claim 35 comprising about 1.0 mg/l benzyladenine, about 0.3 mg/l of indole acetic acid, and about 0.1 mg/l gibberellic acid.

38. The culture medium of claim 35 comprising about 2.0 mg/l benzyladenine, about 0.3 mg/l of indole acetic acid, and about 0.1 mg/l gibberellic acid.

39. The culture medium of claim 35 comprising about 3.0 mg/l benzyladenine, about 0.3 mg/l of indole acetic acid, and about 0.1 mg/l gibberellic acid.

40. The culture medium of claim 33 wherein said rose plant is *Rosa hybrida*.

41. The culture medium of claim 40 wherein said *Rosa hybrida* is selected from the cultivar consisting of Meirutral, Fairy, and Pink Miniwonder.

42. A rose culture comprising a rose stem bearing a node contained in an enclosed vessel containing culture medium comprising about 0.5 to about 3.0 mg/l benzyladenine, 0 to about 1.0 mg/l indole acetic acid, and 0 to about 1.0 mg/l gibberellic acid, wherein said rose culture is capable of generating a flowering rose plant in said enclosed vessel.

43. The rose culture of claim 42 comprising about 0.5 to about 3.0 mg/l of benzyladenine, about 0.3 mg/l of indole acetic acid, and about 0.1 mg/l gibberellic acid.

44. The rose culture of claim 42 comprising about 1.0 mg/l benzyladenine, about 0.3 mg/l of indole acetic acid, and about 0.1 mg/l gibberellic acid.

45. The rose culture of claim 42 comprising about 2.0 mg/l benzyladenine, about 0.3 mg/l of indole acetic acid, and about 0.1 mg/l gibberellic acid.

46. The rose culture of claim 42 comprising about 3.0 mg/l benzyladenine, about 0.3 mg/l of indole acetic acid, and about 0.1 mg/l gibberellic acid.

47. The rose culture of claim 42 wherein said stem bearing a node comprises at least one shoot.

48. The rose culture of claim 42 wherein said rose plant is *Rosa hybrida*.

49. The rose culture of claim 48 wherein said *Rosa hybrida* is selected from the cultivar consisting of Meirutral, Fairy, and Pink Miniwonder.

50. A rose explant selected from the group consisting of a rose stem bearing a node, a rose stem bearing a node and at least one shoot, and a rose shoot, said rose explant contained in an enclosed vessel comprising a culture medium comprising about 0.5 to about 3.0 mg/l benzyladenine, 0 to about 1.0 mg/l indole acetic acid, and 0 to about 1.0 mg/l gibberellic acid, wherein said rose explant is capable of producing a flowering rose plant in said enclosed vessel.

51. The rose explant of claim 50 wherein said rose plant is capable of transfer to soil.

52. The rose explant of claim 50 wherein said rose explant is *Rosa hybrida*.

53. The rose explant of claim 50 wherein *Rosa hybrida* is selected from the cultivar consisting of Meirutral, Fairy, and Pink Miniwonder.

54. A rooting medium for the rooting of rose plants comprising MS medium and about 1 to about 5 mg/l glycine, about 50 to about 150 mg/l myo-inositol, about 0.1 to about 1.0 mg/l nicotinic acid, about 0.1 to about 1.0 mg/l pyridoxine.HCl, about 0.01 to about 0.2 mg/l thiamine.HCl, about 10 to about 50 g/l sucrose, and optionally containing about 1 to about 5 g/l gelling agent, about 0.05 to about 1 mg/l indole butyric acid.

55. The rooting medium of claim 54 further comprising about 0.01 to about 0.2 mg/l naphthaleneacetic acid.

* * * * *

UNITED STATES PATENT AND TRADEMARK OFFICE
CERTIFICATE OF CORRECTION

PATENT NO. : 5,843,782
DATED : December 1, 1998
INVENTOR(S) : Dobres et al.

It is certified that error appears in the above-indentified patent and that said Letters Patent is hereby corrected as shown below:

On the cover page, under "OTHER PUBLICATIONS", first column, at the first instance of "Murashige et al.", please delete "*Physiologian*" and insert --*Physiologia*-- therefor.

On the cover page, under "OTHER PUBLICATIONS", first column, at the first isntance of "Murashige et al.", please delete "p. 473." and insert --pp. 473-497-- therefor.

On the cover page, under "OTHER PUBLICATIONS", second column, at "Ghashghaie et al.", second line thereof, please delete "*Physilogia*" and insert --*Physiologia*-- therefor.

On the cover page, under "OTHER PUBLICATIONS", second column, at "DeVries et al.", please insert --of-- after "Effect" and before "BAP".

On the cover page, under "OTHER PUBLICATIONS", second column, at "Douglas et al.", please delete "Micorpropagation" and insert --Micropropagation-- therefor.

In column 13, claim 26, lines 47-48, please delete "plant s capable" and insert --plant is capable-- therefor.

Signed and Sealed this

Thirty-first Day of August, 1999

*Attest:*

Q. TODD DICKINSON

*Attesting Officer*   *Acting Commissioner of Patents and Trademarks*